United States Patent [19]
Pierce et al.

[11] Patent Number: 5,876,415
[45] Date of Patent: Mar. 2, 1999

[54] MULTI-PLANE CORNEAL INCISION FORM

[75] Inventors: Robert W. Pierce, Wrentham; Edwin G. Lee, Burlington; Dana M. Cote, Billerica, all of Mass.

[73] Assignee: Becton Dickinson and Company, Franklin, N.J.

[21] Appl. No.: 879,867

[22] Filed: Jun. 20, 1997

[51] Int. Cl.⁶ .................................................. A61F 9/00
[52] U.S. Cl. ................................................................ 606/166
[58] Field of Search ................................. 606/166, 161, 606/167, 170, 172; 128/898

[56] References Cited

U.S. PATENT DOCUMENTS

| | | | |
|---|---|---|---|
| 4,739,761 | 4/1988 | Grandon | 606/166 |
| 4,844,060 | 7/1989 | Krumeich | 606/166 |
| 5,080,111 | 1/1992 | Pallin | 128/898 |
| 5,571,124 | 11/1996 | Zelman | 606/166 |

Primary Examiner—Michael Buiz
Assistant Examiner—Kevin Truong
Attorney, Agent, or Firm—Arthur D. Dawson; Eric M. Lee

[57] ABSTRACT

The multi-plane corneal incision form of this invention includes a frame member in the shape of a segment of a hollow sphere that fits over a patient's cornea. The inner surface of the frame member includes a protuberance that distorts the cornea when the frame member is placed against the patient's cornea. The frame member also includes an aperture adjacent to the protuberance to allow a surgical blade to pass therethrough. By carefully configuring the protuberance and aligning the aperture, a physician can insert a surgical blade into the aperture and through the distorted cornea in a planar fashion that results in a multi-plane incision in the cornea once the frame member is removed from contact with the patient's cornea.

7 Claims, 6 Drawing Sheets

MULTI-PLANE CORNEAL INCISION FORM

BACKGROUND OF THE INVENTION

This invention relates to a medical device that is useful in aiding physicians to make complex multi-plane incisions in a patient. More particularly this invention relates to a form that distorts a portion of a patient's body in such a way that allows the physician to make a straight line planar incision in the distorted portion of the patient's body to form a complex multi-plane incision in the patient's body when the form is removed from the patient's body.

In various surgical procedures, the physician typically has to make an incision in the patient in order to remove unwanted tissue, repair damaged tissue, or implant a device to improve the patient's well being. In certain cases, all three of these activities or a combination thereof must be done in a single procedure. For example, in cataract surgery, the physician removes the natural lens that has been clouded by a cataract from the patient's eye and replaces it with an artificial lens that will improve the patient's eyesight. In order to perform this procedure, an incision is made in the cornea or sclera of the eye. This provides the physician with access to the patient's lens. The clouded lens is cut loose and removed. There are a number of different procedures that are used to remove a patient's lens that has a cataract. Two of the more common techniques are known as extracapsular surgery and phacoemulsification. In extracapsular surgery, the physician removes the lens leaving behind the posterior capsule. In phacoemulsification, the physician fragments the lens by ultrasonic vibrations. The lens is simultaneously irrigated and aspirated. After the lens is removed, the physician then inserts an artificial lens known as an intraocular lens (IOL) into the eye behind the iris. Two tiny C-shaped arms connected to the IOL eventually become scarred into the side of the eye and hold the IOL firmly in place.

Although cataract surgery is considered routine, it is not foolproof. For example, the incision through which the devices that are used to perform the procedure are inserted must provide an opening that is substantially the same circumference as the probes and other surgical devices that are used to perform the procedure. This minimizes trauma to the eye and facilitates rapid healing of the eye after the procedure. In addition, in the case of phacoemulsification, if the incision is too small, corneal tissue surrounding the incision may contact the ultrasound probe and be burned. Alternatively, if the incision is too large, leakage from the eye after the procedure may occur causing iris prolapse and subsequently endothelial cell loss.

Another common problem with cataract surgery is suture induced astigmatism. Since an incision is made in the eye to perform the procedure, some mechanism must be used to ensure that the incision remains closed during the healing process to prevent a path for infection into the eye and so that the eye heals properly. In the past, sutures have been used to close the incision. However, the use of sutures in the eye to seal the incision after the cataract surgery may alter the shape of the eye. Such an alteration of the shape of the eye may result in astigmatism. In addition, the use of sutures may cause other complications such as eye irritation, suture abscesses, suture extrusion and foreign body reaction, In an effort to avoid the use of sutures in cataract surgery, new sutureless techniques have been developed. These sutureless techniques involve the same standard procedures used to remove the cataract and implant the IOL but require the physician to make an incision in the eye having a particular shape or geometry. By making an incision having a particular geometry, the normal internal pressure in the eye pushes against the eye at the location of the incision to keep the incision closed.

One particular sutureless technique that is currently being used is known as the clear cornea approach and requires a particular incision that is self-sealing to be made in the eye. The shape of one particular incision comprises a pair of contiguous circular segments that have their centers of radius on opposite sides of the incision, i.e. the incision has a substantially S shaped geometry. Unfortunately, because of the complex, multi-plane geometry of the incision, it is difficult to form consistently. This problem is especially acute for new physicians and physicians who do not perform this technique often enough to maintain their proficiency. If such incisions are improperly formed, a number of complications can occur. For example, endophthalmitis, induced astigmatism, damage to the cornea, the iris or other intraocular tissue can occur, and impaired intraoperative vision of the physician can result.

SUMMARY OF THE INVENTION

It is therefore an object of this invention to provide a mechanism that facilitates the formation of a complex multi-plane incision geometry into a portion of a patient's body.

It is another object of this invention to eliminate complications that may arise from poorly constructed incisions in a portion of a patient's body.

It is a still further object of this invention to provide a form for use in ophthalmic surgery that allows a physician to make precise incisions in a patient's eye so the physician can perform the clear cornea technique with a high degree of proficiency.

The multi-plane corneal incision form of this invention includes a frame member, with a handle attached thereto, in the shape of a segment of a hollow sphere that fits over a patient's cornea. The inner surface of the frame member includes a protuberance that distorts the cornea when the frame member is placed against the patient's cornea and pressure is applied to the frame member and/or a vacuum is applied to the cornea to pull the cornea against the inner surface of the frame member. The frame member also includes an aperture adjacent to the protuberance to allow a surgical blade to pass therethrough. In this manner, when a physician inserts a surgical blade into the aperture in a linear fashion through the distorted cornea, the physician is actually making an incision in the cornea having a complicated, multi-plane geometry.

Although this invention is described in this document as a multi-plane corneal incision form, it is to be understood that this invention is not limited to cataract surgery or even to ophthalmic surgery. This invention also has applicability to other types of surgery in other areas of the body that are deformable where a complex, multi-plane incision is to be made by the physician. For example, this invention may be applied in the areas of vascular surgery or implant surgery.

The above and other objects and advantages of the invention will be apparent upon consideration of the following detailed description.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
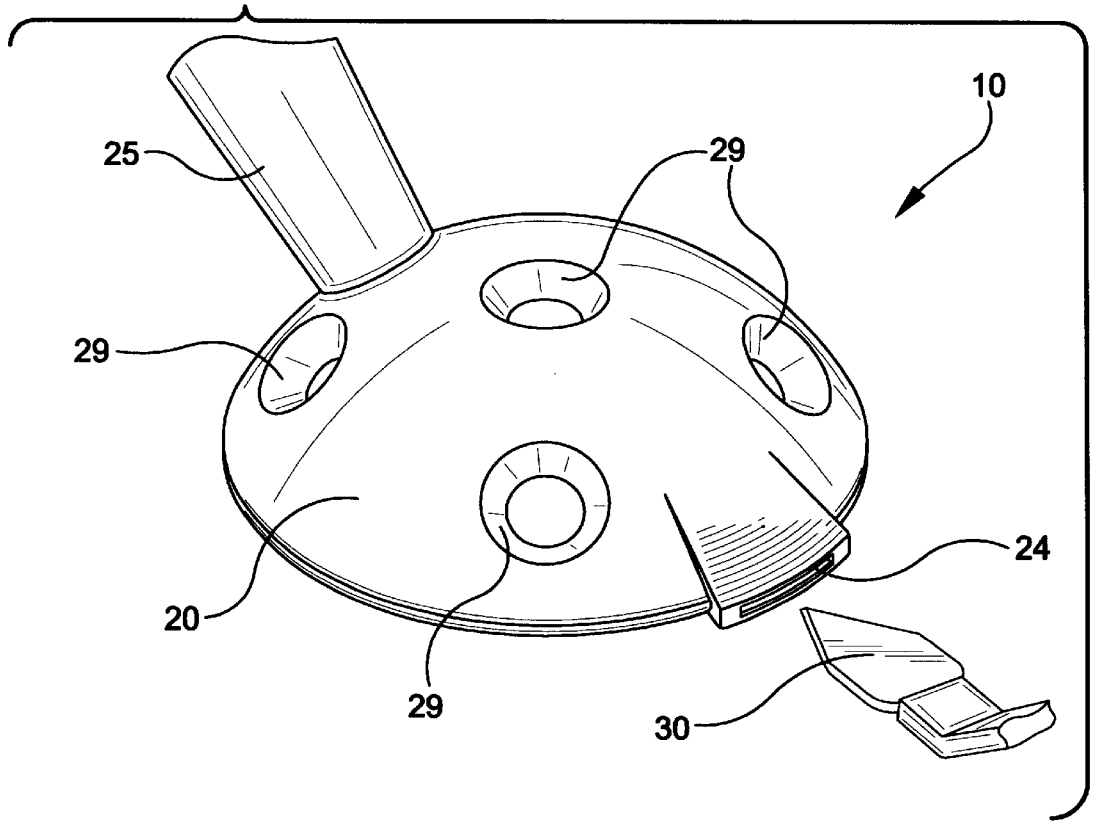
FIG. 1 is a perspective view of the multi-plane corneal incision form of this invention showing the outer surface of the frame member and a portion of an ophthalmic scalpel that will be used to make the incision with the help of the multi-plane corneal incision form.
Figure 2:
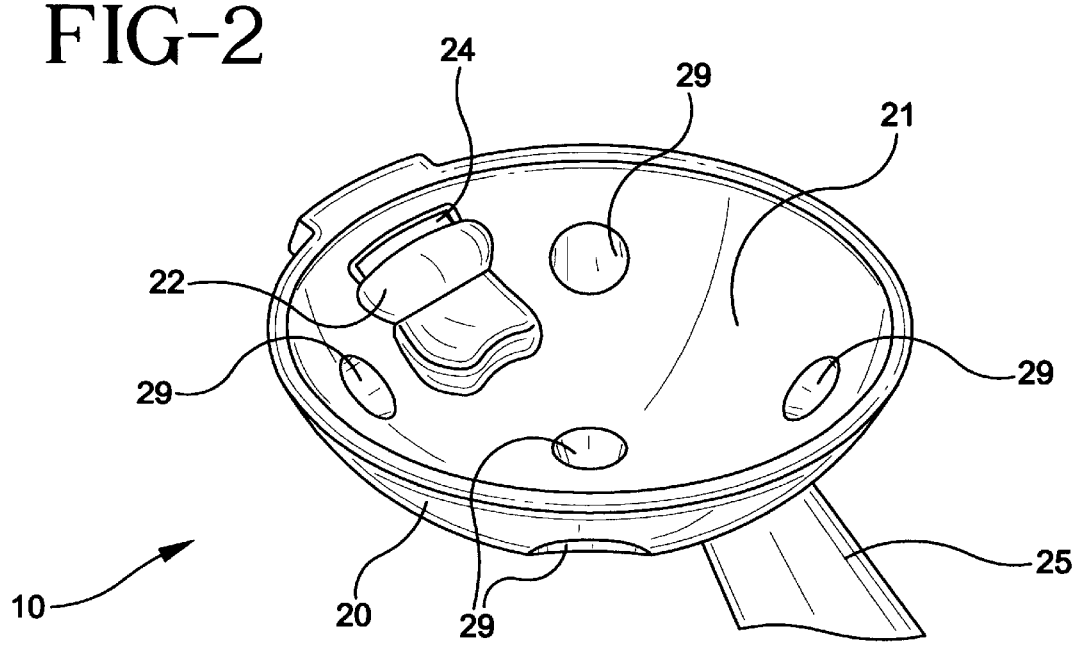
FIG. 2 is a perspective view of the multi-plane corneal incision form of this invention showing the inner surface of the frame member with the protuberance therein.
Figure 3:
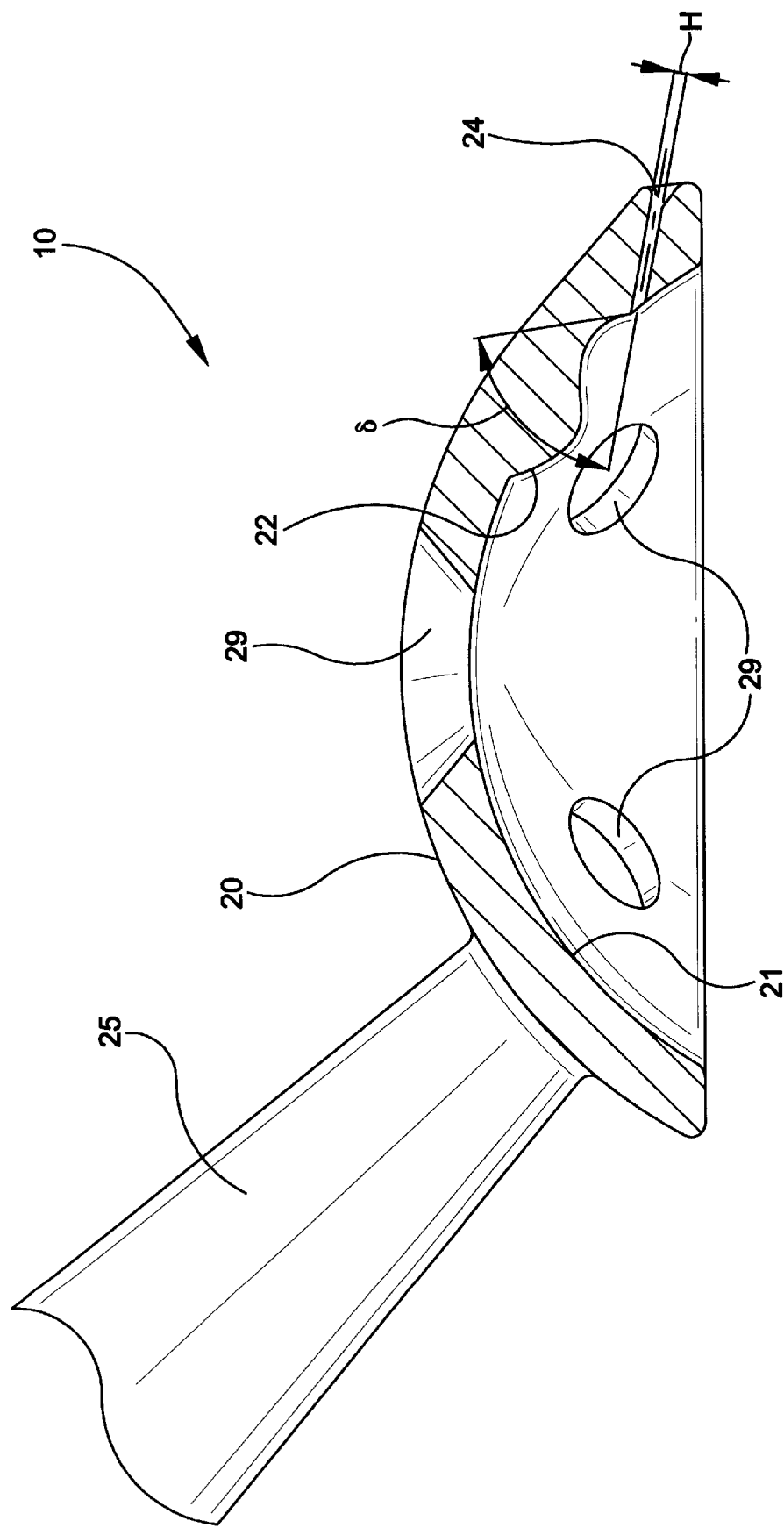
FIG. 3 is a cross-sectional view of a portion of the multi-plane corneal incision form of this invention.
Figure 4:
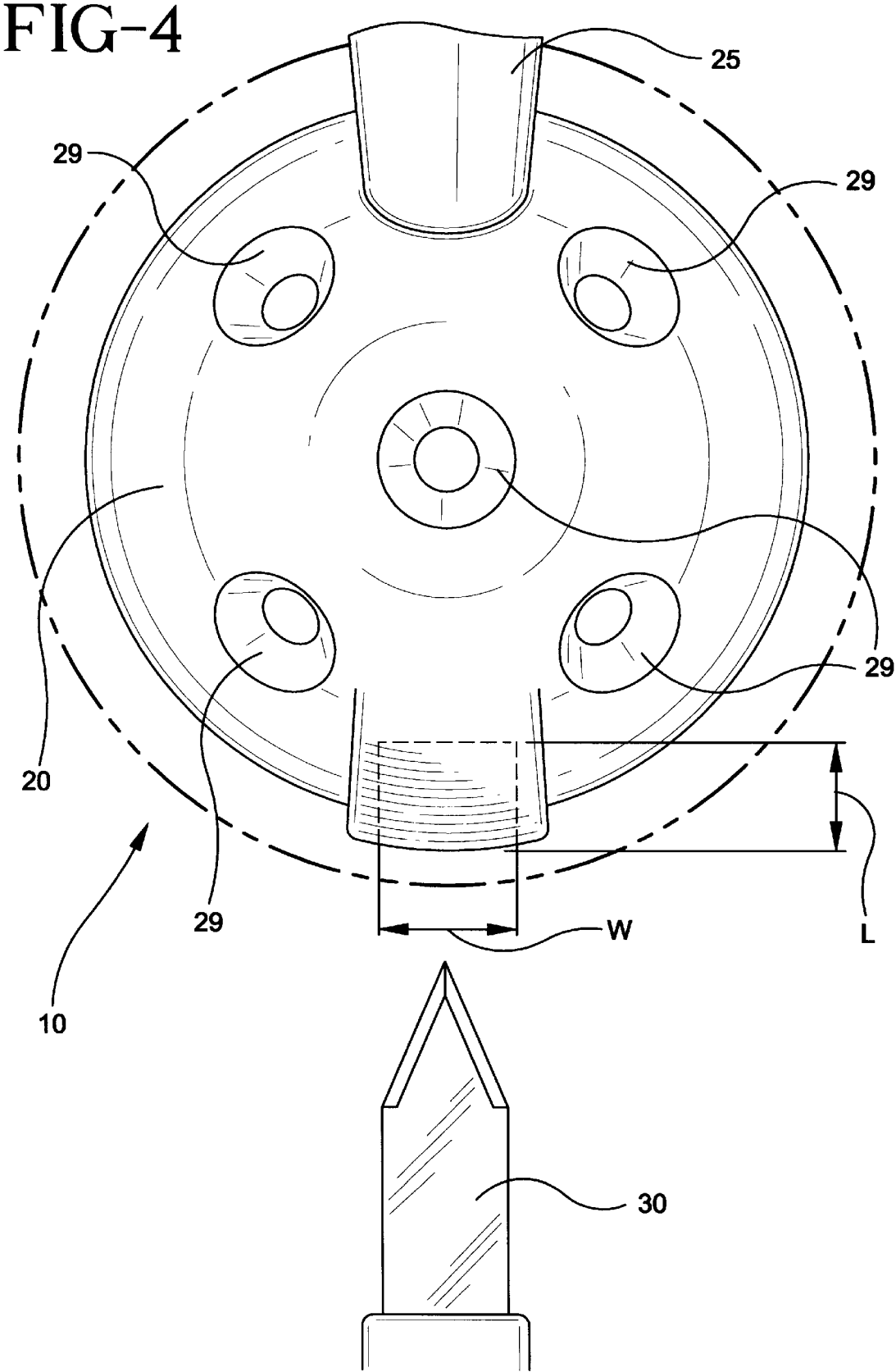
FIG. 4 is a top plan view of the multi-plane corneal incision form of this invention and a portion of an ophthalmic scalpel oriented for use with respect to the multi-plane corneal incision form.

The multi-plane corneal incision form 10 of this invention includes a frame member 20, with a handle 25 attached thereto, in the shape of a segment of a hollow sphere that fits over a patient's cornea. Frame member 20 preferably defines a plurality of holes 29 therein to allow the physician to easily visualize the surface of the eye. In addition, holes 29 provide access to the patient's eye for irrigation during the procedure or to allow suction to be exerted against the eye to ensure that it is fully compressed against frame member 20. Alternatively, frame member 20 could be made from clear plastic and be devoid of holes 29. This would allow the physician to visualize the eye and allow a separate vacuum mechanism, not shown, to be applied to frame member 20. Such a vacuum mechanism pulls the eye tightly against frame member 20 by suction. This force, either with or without the pressure placed against frame member 20, ensures that the eye remains properly located with respect to frame member 20, i.e. fixated, during the surgical procedure. Frame member 20 could also include a number of markings thereon to allow the physician properly to orient multi-plane corneal incision form 10 on the eye.

The inner surface 21 of frame member 20 includes a protuberance 22 that distorts the cornea when frame member 20 is placed against the patient's cornea and pressure, and/or a vacuum, is applied. Frame member 20 also includes an aperture 24 adjacent to protuberance 22 to allow a surgical blade 30 to pass therethrough. In this manner, when a physician inserts surgical blade 30 into aperture 24 in a linear fashion through the distorted cornea, the physician is actually making an incision in the cornea having a complicated, multi-plane geometry.

In the case of the clear cornea incision, typically blade 30 is a keratome or slit blade. These blades have a spear shaped, beveled sharp tip and dull parallel sides. Aperture 24 should be sized to allow blade 30 to extend into aperture 24 a sufficient distance so the cutting surface of blade 30 extends into the anterior chamber of the patient's eye. However, there should not be so much clearance between the surfaces defining aperture 24 that blade 30 can easily be rotated or tilted in aperture 24. Thus the width (W) and height (H) of aperture 24 should be substantially equal to the width and height of surgical blade 30. Preferably width (W) should be only about 0.05 millimeters wider than the width of blade 30 and height (H) should be only about 0.01 millimeters thicker than the height of blade 30. The length (L) of aperture 24 should only be as long as is necessary to properly direct blade 30 through the distorted portion of the cornea. In addition, the length (L) of aperture 24 should not be so long as to interfere with the ability of blade 30 to create an incision of the proper length in the cornea. The entire distal cutting surface of blade 30 should be exposed inside frame member 20 a distance greater than the length of the incision (P) past aperture 24 when blade 30 is inserted to the hilt into aperture 24 to provide an incision of the appropriate architecture.

Figure 6:
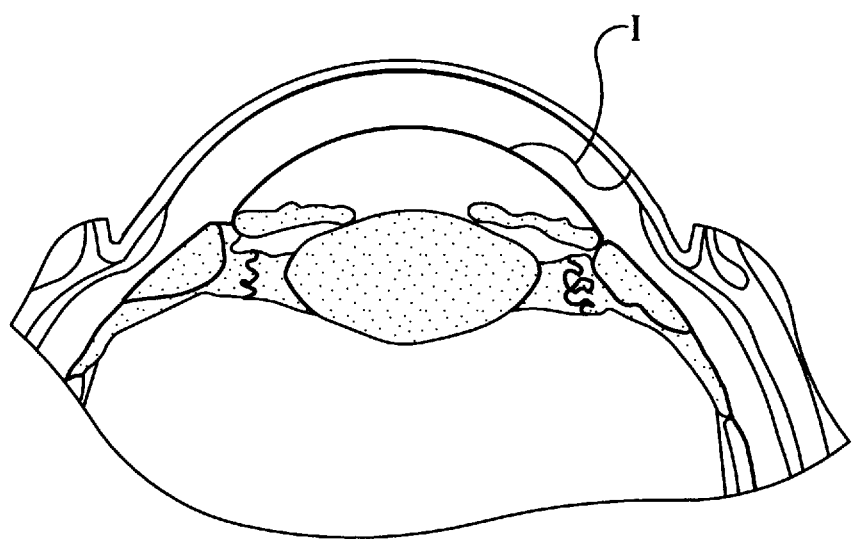
FIG. 6 is a cross-sectional view of a patient's cornea showing an incision resulting from the use of the multi-plane corneal incision form of this invention.
Figure 7:
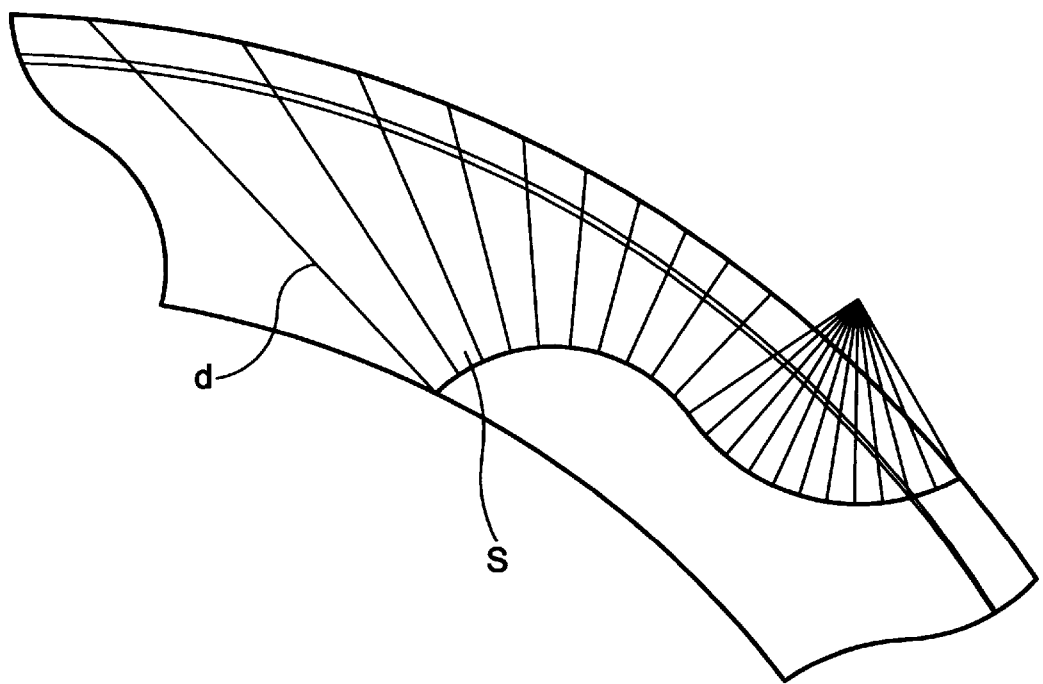
FIG. 7 is a schematic view of a portion of the patient's eye showing the geometry of an incision made with the multi-plane corneal incision form of this invention and the method for translating the incision geometry to the multi-plane corneal incision form of this invention.

The exact shape of protuberance 22 and the exact position of aperture 24 in relation to protuberance 22 depends on the geometry of the incision that must be made in the patient. In the case of one type of incision for the clear cornea procedure, the incision (I) that must be made in the patient's cornea comprises two contiguous circular segments having centers of curvature on opposite sides of the segments, i.e. the incision is a substantially S shaped curve. The circular segment adjacent to the outer surface of the cornea is concave while the circular segment adjacent to the inner surface of the cornea is convex. See FIGS. 6, 7 and 9. In addition, the angle α that the incision makes with the tangent line at the point where the incision contacts the outer surface of the cornea is 750 and the angle β that the incision makes with the tangent line at the point where the incision contacts the inner surface of the cornea is 53°. The shape of protuberance 22 and the position of aperture 24 must allow the physician to make this incision using multi-plane corneal incision form 10 and a linear cut with blade 30.

In order to form protuberance 22 into the appropriate shape, protuberance 22 must distort the cornea, or some other portion of the body where the incision is to be made, in such a way that a straight line, i.e. planar, incision in the distorted portion of the cornea results in an incision having the proper geometry when the cornea is no longer distorted. It has been surprisingly determined that the appropriate geometry of protuberance 22 can be determined that will allow the physician to form the appropriate incision by using the distances between the outer surface of the cornea and the incision measured along lines perpendicular to tangents to the incision at various locations along the incision.

In order to accurately transfer the geometry of the incision to protuberance 22 the length of the incision first must be determined. This length can be determined by using appropriate geometrical theorems for the particular geometry of the incision under investigation. In the case of the clear cornea incision, the length can be determined by determining the length of the two arcs that form the incision. Since the radii (R) and the angles (A) of the arcs are known, the length of each arc can be determined by using the following formula:

$$S = R \times \text{rad } A.$$

Figure 8:
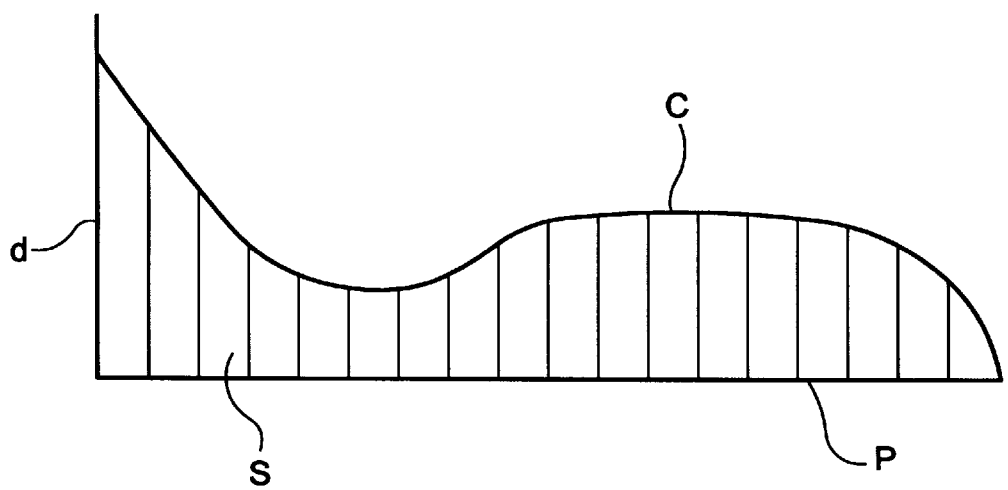
FIG. 8 is a schematic drawing showing the shape of the incision in FIG. 7 that is to be made in the patient's eye translated onto a straight line to facilitate the manufacture of an appropriate form to aid the physician in making the complex, multi-plane incision.

Once the length of the incision is determined, a straight line is formed having the length of the incision. This straight line (P) represents inner surface 21. Next, the incision and straight line are divided into an equal number of segments (S). See FIGS. 7 and 8. The number of segments that should be used will be discussed in detail hereinafter. Next, the distance (d) from the incision to the outer surface of the cornea is determined for each segment (S). These varying distances (d) are measured along a straight line that is perpendicular to a tangent line to a point on the incision in the segment being studied. These distances (d) are then laid along the straight line for each segment (S). Finally, a smooth curve (C) is formed connecting the ends of the various distances (d) extending from the straight line. This resulting curve (C) represents the geometry of protuberance 22 extending from inner surface 21 of frame member 20. It will be apparent that a sufficient number of segments (S) must be used to ensure that a smooth curve (C) can be fitted onto the ends of the various distances (d) extending from the straight line (P). If too few segments (S) are used, the resulting curve (C) will not be smooth and will not provide a sufficiently accurate transposition for the incision geometry to protuberance 22. The number of segments (S) used can be determined by simple routine experimentation. In the case of the clear cornea incision and protuberance 22, eighteen segments (S) are used. It is important to note that because the distance (d) is measured from the incision to the outer surface of the cornea, the curvature of the cornea is taken into account when forming the geometry of protuberance 22 since inner surface 21 has a curvature substantially equal to the curvature of the cornea and the curve C is applied along inner surface 21. To facilitate the creation of protuberance 22, any standard computer aided drafting software can be used.

Figure 5:
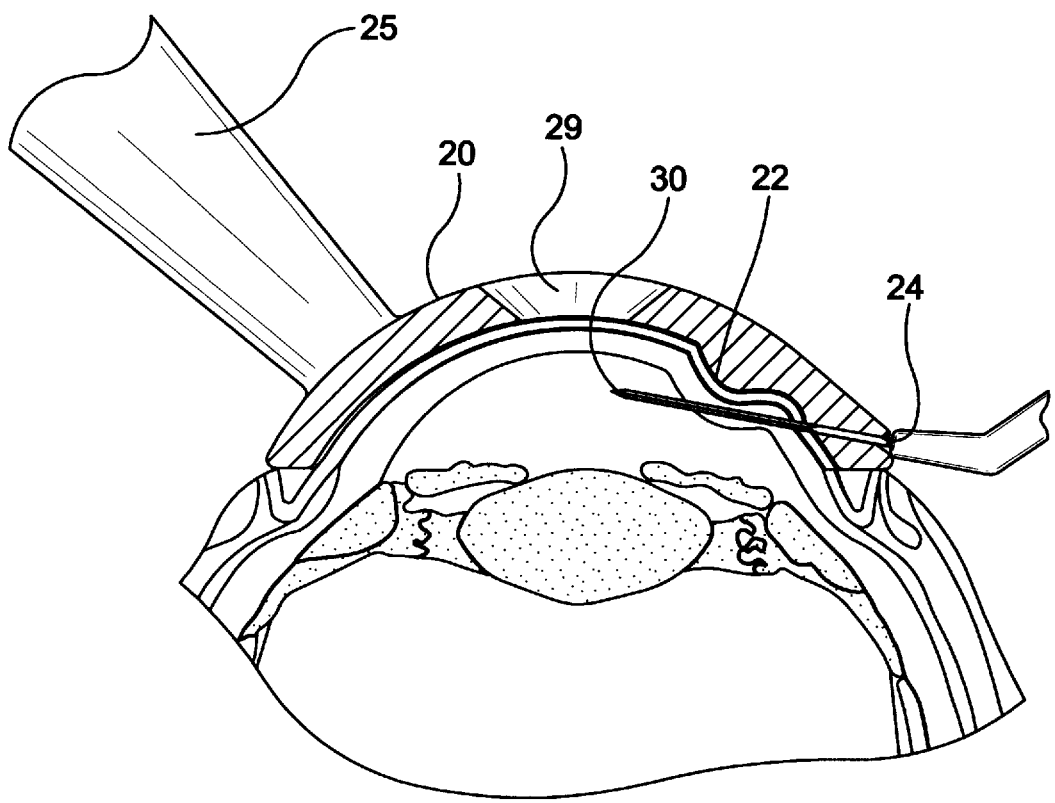
FIG. 5 is a cross-sectional view of the multi-plane corneal incision form of this invention placed against a patient's eye, thereby distorting a portion of the eye, and showing a portion of an ophthalmic scalpel making a straight line, i.e. planar, incision in a portion of the eye with the aid of the multi-plane corneal incision form.
Figure 9:
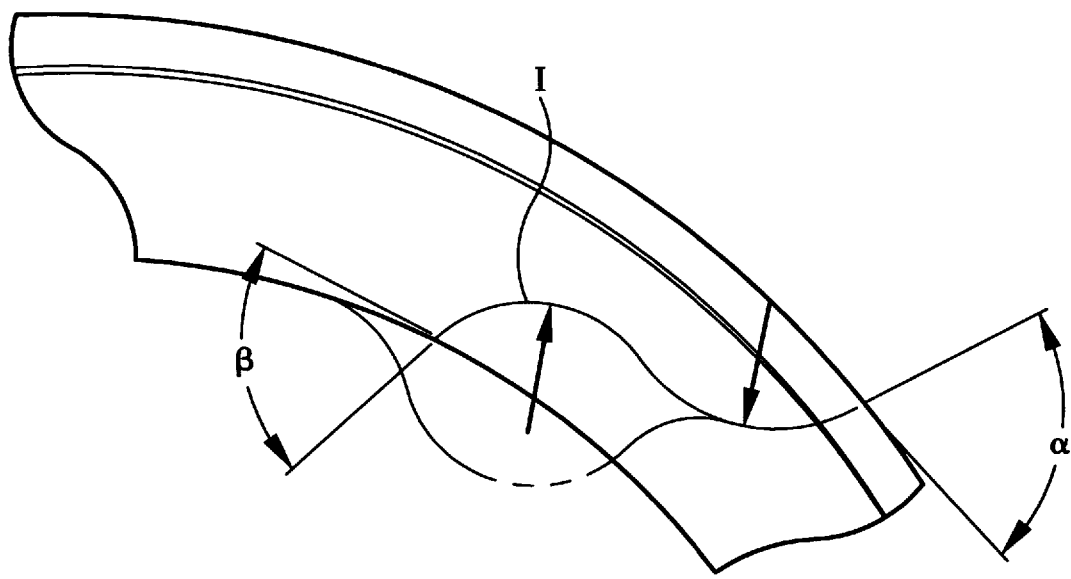
FIG. 9 is a schematic view of a portion of the patient's eye with the incision formed therein showing the movement of the eye caused by the multi-plane corneal incision form of this invention.

As seen in FIGS. 5 and 9, protuberance 22 distorts the cornea in such a way that when a straight line, i.e. planar incision is made in the distorted cornea, the resulting incision has a complex, multi-planar geometry when protuberance 22 is removed from the cornea and the cornea is no long distorted.

Once the geometry for protuberance 22 is determined, the orientation and location of aperture 24 must be determined. Again, the exact orientation and location of aperture 24 depends on the incision that is to be made in the patient. In the case of the clear cornea incision, since the angle that the incision makes to the tangent to the cornea at the point where the incision crosses the outer surface of the cornea is 75°, the angle δ formed between the longitudinal axis of aperture 24 and the tangent to the point where aperture 24 crosses inner surface 21 of frame member 20 should be the same angle. In addition, the point where aperture 24 crosses inner surface 21 of frame member 20 should be coterminous with the point on protuberance 22 that represents the start of the incision on the cornea. By properly forming protuberance 22, the angle that the incision makes to the tangent to the cornea at the point where the incision crosses the inner surface of the cornea will be the desired angle for the clear cornea incision.

Thus it is seen that a mechanism is provided that facilitates the formation of a complex incision geometry into a portion of a patient's body so as to eliminate complications that may arise from poorly constructed incisions in a portion of a patient's body and a form is provided for use in ophthalmic surgery that allows a physician to make precise incisions in a patient's eye so the physician can perform the clear cornea technique with a high degree of proficiency.

We claim:

1. A multi-plane corneal incision form, comprising:
    a frame member having an inner surface with a configuration that is generally in the shape of a segment of a hollow sphere, wherein the frame member defines an aperture therein to allow a surgical blade to be inserted through the frame member past the inner surface;
    a protuberance affixed to the inner surface of the frame member adjacent to the aperture; and
    a handle affixed to the frame member.

2. The multi-plane corneal incision form of claim 1 wherein the aperture has a proximal opening, a longitudinal axis and a distal opening coterminous with the protuberance.

3. The multi-plane corneal incision form of claim 2 wherein the longitudinal axis of the aperture forms an angle with the inner surface of about 75°.

4. The multi-plane corneal incision form of claim 1 wherein the protuberance has a multi-plane topography.

5. The multi-plane corneal incision form of claim 4 wherein the protuberance defines a substantially S shaped cross-section.

6. A multi-plane corneal incision form, comprising:
    a frame member having an inner surface, wherein the frame member defines an aperture therein to allow a surgical blade to be inserted through the frame member past the inner surface;
    a means on the inner surface of the frame member for distorting a portion of a patient's body on which the frame member is placed to allow a blade to be inserted into the aperture in a linear fashion to cut a multi-plane incision in the portion of the patient's body; and
    a handle affixed to the frame member.

7. A method for making a surgical form, comprising:
    identifying the geometry of an incision to be made in a patient;
    dividing the incision into a plurality of equal segments;
    determining a distance between the incision and an outer surface of the patient measured along a line perpendicular to a tangent point on the incision to the outer surface of the patient for each of the plurality of equal segments into which the incision is divided;
    determining the length of the incision;
    forming a straight line having a length equal to the length of the incision;
    dividing the straight line into the plurality of equal segments into which the incision is divided;
    measuring the distance from the straight line for each segment;
    connecting the end points of each of the distances from the straight line with a protuberance line; and
    forming a surface extending from an inner surface on the surgical form that follows the protuberance line.

* * * * *